United States Patent [19]

Williams

[11] Patent Number: 4,824,641

[45] Date of Patent: Apr. 25, 1989

[54] CAROUSEL AND TIP

[75] Inventor: Fred G. Williams, San Anselmo, Calif.

[73] Assignee: Cetus Corporation, Emeryville, Calif.

[21] Appl. No.: 877,026

[22] Filed: Jun. 20, 1986

[51] Int. Cl.⁴ ............................................. G01N 35/06
[52] U.S. Cl. .................................. 422/100; 73/864.12; 422/63; 422/65; 422/73
[58] Field of Search .................. 73/864.01, 864.12; 422/99, 100, 63–67, 73

[56] References Cited

U.S. PATENT DOCUMENTS

| Re. 29,376 | 8/1976 | Hiszpanski | 285/169 |
|---|---|---|---|
| 561,441 | 6/1896 | Schmidt . | |
| 570,890 | 11/1896 | Baird . | |
| 798,441 | 8/1905 | Nelson . | |
| 1,742,497 | 1/1930 | Dickinson . | |
| 1,913,246 | 6/1933 | Saine . | |
| 2,386,562 | 10/1945 | Mahoney | 285/180 |
| 3,129,020 | 4/1964 | Bujnowski | 285/110 |
| 3,199,300 | 8/1965 | Fiore | 61/53 |
| 3,494,201 | 2/1970 | Roach | 73/425.6 |
| 3,554,580 | 1/1974 | Goyke et al. | 285/260 |
| 3,646,817 | 3/1972 | Hinchman et al. | 73/425.6 |
| 3,707,972 | 1/1973 | Villari et al. | 128/349 R |
| 3,732,734 | 5/1973 | Avakian | 73/425.6 |
| 3,760,639 | 9/1973 | Sokol et al. | 73/425.6 |
| 3,853,217 | 12/1974 | Scordato et al. | 206/223 |
| 3,918,308 | 11/1975 | Reed | 73/425.6 |
| 3,985,032 | 10/1976 | Avakian | 73/425.4 P |
| 4,023,716 | 5/1977 | Shapiro | 222/309 |
| 4,054,062 | 10/1977 | Branham | 73/425.6 |
| 4,072,330 | 2/1978 | Brysch | 285/239 |
| 4,151,750 | 5/1979 | Suovaniemi et al. | 73/425.6 |
| 4,152,017 | 5/1979 | Abramson | 285/260 |
| 4,187,724 | 2/1980 | Citrin | 73/425.4 P |
| 4,215,092 | 7/1980 | Suovaniemi et al. | 422/100 |
| 4,252,117 | 2/1981 | Sheehan | 128/214 R |
| 4,287,155 | 9/1981 | Tersteg | 422/64 |
| 4,362,064 | 12/1982 | d'Autry | 73/864.13 |
| 4,418,580 | 12/1983 | Satchell et al. | 73/864.13 |

FOREIGN PATENT DOCUMENTS

| 0034438 | 8/1981 | European Pat. Off. . |
| 2114108 | 11/1971 | Fed. Rep. of Germany . |
| 2021566 | 7/1970 | France . |
| 2313982 | 6/1976 | France . |
| 7509286 | 10/1976 | France . |

Primary Examiner—Michael S. Marcus
Attorney, Agent, or Firm—William H. Benz; Albert P. Halluin

[57] ABSTRACT

An improved sample carrier and pipette tips for use in an automated sample handling device are disclosed. This carrier mounts on and is removable from a carousel and has spaced about the circumference of its body a plurality of apertures for receiving the sample containers. Each aperture has on its interior side, that is its axis side, an intruding resilient finger which is deflected when a sample container is inserted into the aperture and which applies pressure on the sample container forcing it against the outside edge of the aperture and preventing inadvertent rotation of the sample container within the aperture. In the most common embodiment the apertures are substantially parallel to the axis of the circular body of the carrier so that they can be accessed by sample-handling equipment moving perpendicular to the plane of rotation of the carousel. In another embodiment the apertures are angled in a posture where they can undergo angled centrifugation, if desired. The sample carrier is also adapted to carry a plurality of pipette tips for sequential pick up by an automated pipette. Pipette tips particularly adapted for automatic pick up are also disclosed.

5 Claims, 3 Drawing Sheets

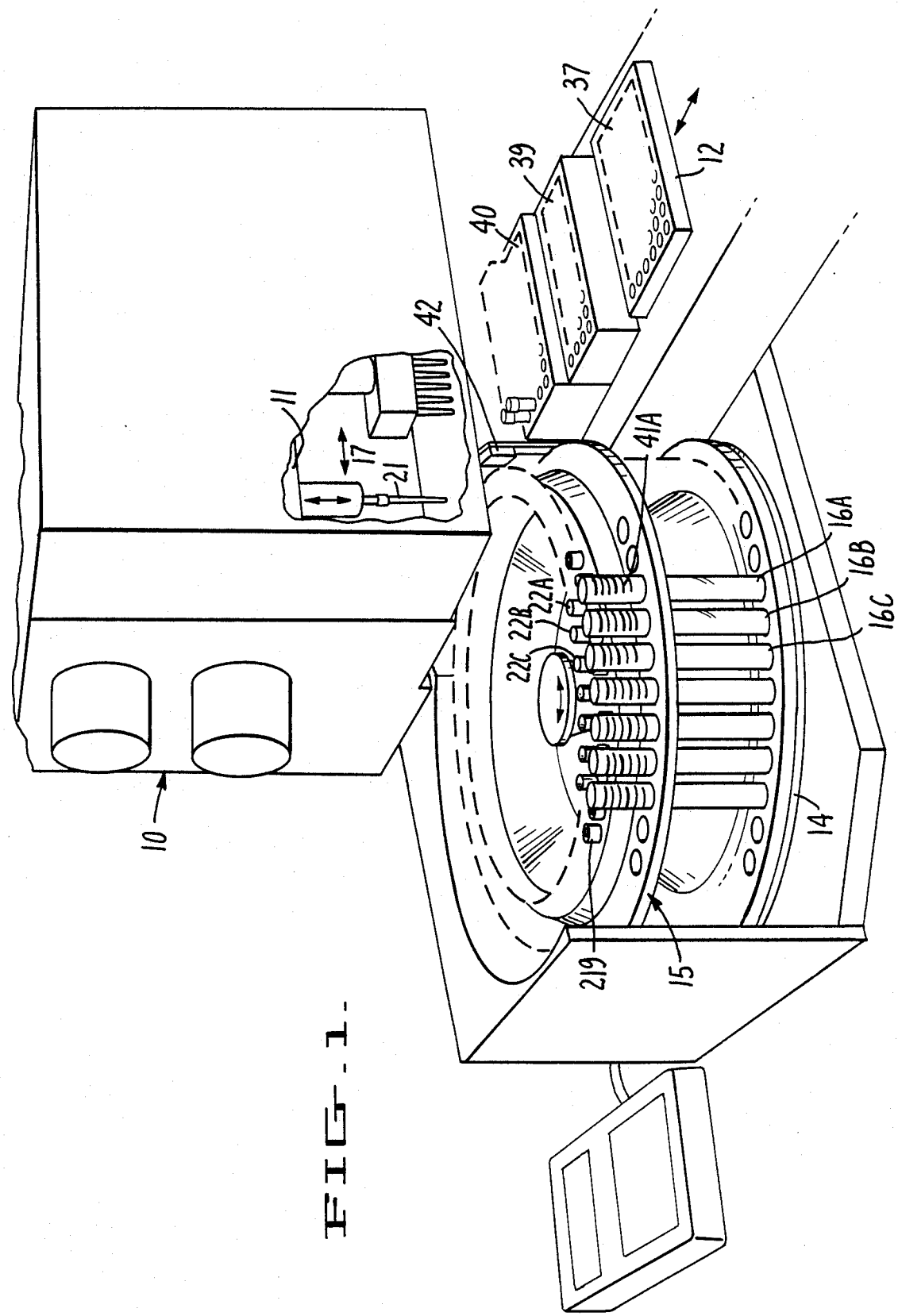
FIG._1_

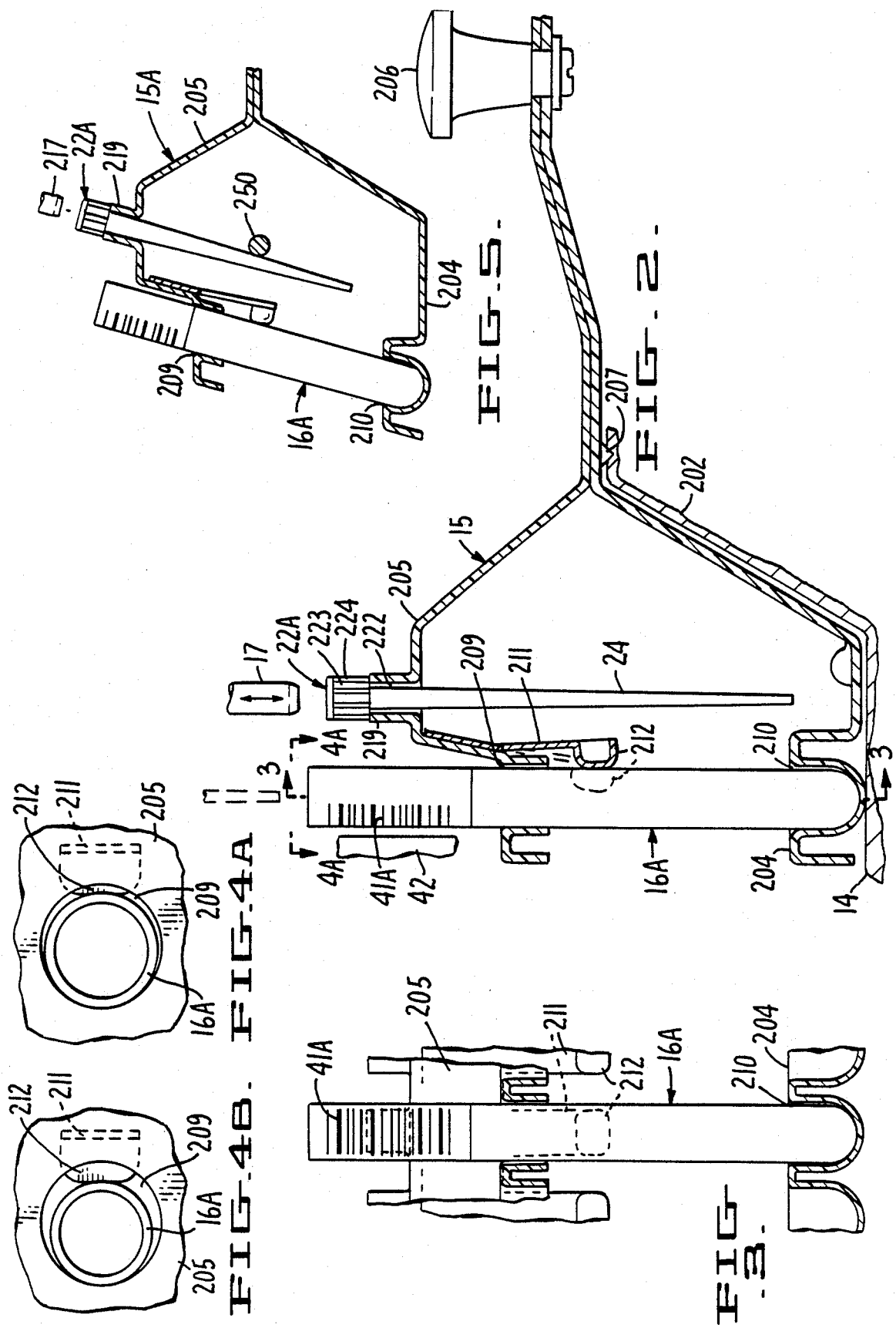

CAROUSEL AND TIP

BACKGROUND OF THE INVENTION

Field of the Invention

The present invention relates to machines for automatically manipulating small liquid samples in a chemical analysis setting. More particularly, it relates to improvements in sample carousels and the use of these carousels in combination with improved pipette tips for transferring liquid to or from these carousels.

Background Information

Chemical and biochemical anaylses are designed to detect the presence or quantity of a given chemical or species in a sample. In a clinical or medical laboratory setting one common test regimen involves contacting each of a plurality of aliquots of the sample with a different reagent or combination of reagents and detecting a characteristic reaction or change in physical state to indicate the presence of a particular chemical or species. One such application is blood typing where a sample of blood is spun in a centrifuge to give serum and blood cell fractions and a plurality of portions of these two materials are contacted with various reagents to determine type via specific cell agglutination. Many other test regimens involve the same general processes of centrifugation, dispensing and the like. Another such application involves antigen/antibody screening tests where a sample of a body fluid such as plasma, serum, blood, urine or the like is contacted with a plurality of antigen- and/or antibody-containing reagents and the formation of immune complexes between species in the body fluid and the reagents is detected.

It will be appreciated that such screening type tests can involve the repetitive dispensing and manipulation of numerous small liquid volumes. Each sample may be screened against many reagents and in a medical laboratory setting there may be a large number of samples undergoing analysis at any given time.

It is desirable, of course, to perform such repetitive assays as quickly and efficiently as possible. It is also desirable to use limited sample size to cut down on expensive reagent use and to minimize the volume of sample—e.g., blood—that must be taken from the patient. The need for speed and efficiency and the use of small volumes have given rise to a range of techniques wherein the assays are carried out in small volume wells in assay trays. Typically, such trays contain 20, 24, 48 or 96 wells arranged in a rectangular configuration. A range of devices are now available to facilitate the addition of materials to these multiwell trays. These devices can be manual, semiautomated or automated and can in some cases be computer controlled with programs which allow several sequential manipulations to be performed on the samples or test well contents.

A series of United States patents and applications for patents commonly assigned herewith have dealt with a family of automatic sample handling machines marketed b Cetus Corporation of Emeryville, Calif. under the trademarks "ProPette" and "ProGroup." (See, for example, U.S. Pat. No. 4,478,094; U.S. Ser. No. 542,113; U.S. Ser. No. 656,234; U.S. Ser. No. 683,264, U.S. Ser. No. 692,015; and U.S. Ser. No. 752,449; all of which are incorporated herein by reference.) These machines can include a sample carousel which, upon rotation, brings a series of samples into alignment with a pipette which can automatically lower into the sample container to take up a sample for accurate dispensing. To avoid contamination from sample to sample, the pipette is equipped with a disposable tip which can be automatically attached to the pipette and which can take up, store and dispense a sample and then be changed as the next sample is brought into position for dispensing. These machines can contain various devices such as optical scanner bar code readers to recognize and record the samples being dispensed.

It will be appreciated by those involved in this field that there are substantial difficulties raised by the number and differences in format of samples and the number of manipulations performed upon them in a commercial laboratory setting. Record keeping can be confused, equipment can go out of close alignment, and samples can be mishandled at every juncture. It is a general object of this invention to improve the efficiency of liquid sample handling in a laboratory setting.

It is another object of this invention to provide improved sample carriers for carousel type devices.

It is a further object of this invention to provide improved pipette tips which can work in combination with the carrier to facilitate the take up and discharge of liquids from samples with minimal chances of contamination.

STATEMENT OF THE INVENTION

It has now been found that the efficiency of an automated sample handling device can be increased by incorporating into it a sample carousel which includes an improved sample carrier. The efficiency of these automated sample handling devices can be further improved when this carrier is adapted to carry a plurality of pipette tips for automated pick up by the pipette. These pipette tips can be adapted to facilitate their automated pick up, as well. More specifically, the improved carrier for the samples is characterized by being round in shape and by being adapted for use with a rotatably positionable carousel for successively delivering a series of sample containers to an analysis station. This carrier is removable from the carousel and has spaced about the circumference of its body a plurality of apertures for receiving the sample containers. Each aperture has on its interior side, that is its axis side, an intruding resilient finger which is deflected when a sample container is inserted into the aperture and which applies pressure on the sample container forcing it against the outside edge of the aperture and preventing inadvertent rotation of the sample container within the aperture. This locking of the sample container is of special advantage when the sample container carries information to be optically scanned in an optical scanner because the finger not only prevents the container from inadvertently rotating thus taking this information out of position but also forces the sample containers into a consistent position such that when the sample container is brought into the scanner its information is in the focal plane of the scanner.

In the most common embodiment of this invention the apertures are substantially parallel to the axis of the circular body of the carrier so that they can be accessed by sample-handling equipment moving perpendicular to the plane of rotation of the carousel. In another embodiment the apertures are angled with their tops toward the axis of the circular body. This inward tilt places the carriers in a posture where they can undergo angled centrifugation, if desired. This can be carried out by mounting the carrier upon a centrifuge for spinning about the axis of the carrier. This can permit samples, such as blood samples, to be centrifuged and automatically sampled thereafter without the need for labor-intensive manual transfer of the individual samples from one piece of equipment to another. In a more comprehensive implementation of this embodiment, the carousel itself is capable of rotating at centrifuge speed as well as stepwise, so that centrifugation and sample positioning can both be automatically programmed and carried out without operator intervention. In this case, a suitable protective enclosure for the carousel and carrier would be provided.

In an additional aspect, the sample carrier of this invention can also include a plurality of pipette tip-receiving and suspending hollow collars. These are located on the carrier body adjacent to the apertures. In this embodiment, the body upon which the collars are located is advantageously fabricated of a plastic material such that the carrier resiliently deflects when a force is applied axially along a pipette tip suspended within said collar. This allows the carrier itself to compensate for variations or misalignments which may occur when a plurality of tips are sequentially picked up by an automated pipette. This automatic pick up is also facilitated when the internal diameter of the hollow collars is substantially greater than the external diameter of the tube of the pipette tip but substantially smaller than the external diameter of the tip collar. This arrangement again permits the automated pick up of tips even when there is substantial variation or misalignment of the system.

In additional aspects, this invention provides disposable pipette tips for automatic attachment to and use with this type of system. These tips are characterized as having bell-mouthed attachment collars and as having at least one circumferential seal located on the inside surface of their the attachment collars. This seal has an internal diameter large enough to receive a bevel-ended or round ended nozzle of the pipette when automatically inserted and small enough to form an automatically-breakable uptake vacuum- and discharge pressure-tight seal with the pipette nozzle when the pipette nozzle is inserted past its beveled end. In preferred embodiments, these tips additionally include on the internal diameter of their attachment collars alignment means for guiding the pipette tip into an axially aligned seal with the pipette nozzle. Such means can include an alignment ring which can also serve as a secondary seal. The tips can also include a positive stop such as an internal shoulder to precisely control the distance to which the pipette end inserts into the tip. In yet an additional embodiment, the inside of the pipette-receiving collar and the outside of a bevel-ended pipette are correspondingly stepped so that the tip is aligned and attached to the pipette substantially simultaneously and immediately after the bevel end of the pipette nozzle is inserted past the internal circumferential seal inside the tip collar and at detachment, both release substantially simultaneously.

BRIEF DESCRIPTION OF THE DRAWINGS

In this specification, reference will be made to the accompanying drawings in which:

FIG. 1 is a perspective view of an automated sample handling device showing the sample carrier and the context in which it and the pipette tips are employed;

FIG. 2 is a cross-sectional detail of the outside edge of the sample carrier made through a sample aperture and through a pipette tip suspending collar;

FIG. 3 is a sectional view taken along line 3—3 of FIG. 2;

FIGS. 4A and 4B are alternative downward views taken along lines 4—4 of FIG. 2 with larger and smaller sample containers respectively;

FIG. 5 is a detail view of an alternative embodiment taken across the carrier in the same position as FIG. 2;

DETAILED DESCRIPTION OF THE INVENTION

Figures 6A, 6B, 6C:
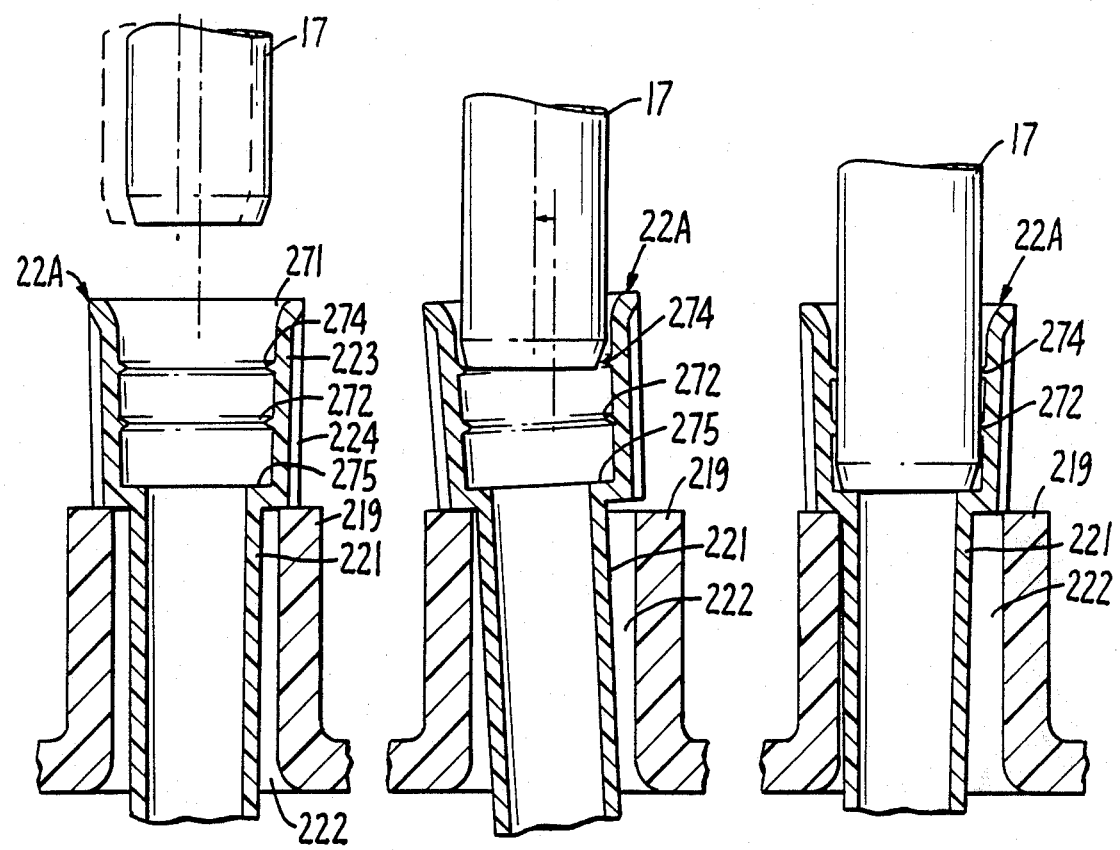
FIGS. 6A, 6B, and 6C are a time sequence showing in cross-section the seating of a pipette into a pipette tip.

Referring now to the drawings, in which similar characters of reference are used in the various figures to designate corresponding parts, FIG. 1 shows a representative overall sample handling system or machine in which the improvements of this invention can find application. This machine 10 includes a vertically translatable carriage 11 positioned above a horizontally translatable table 12. FIG. 1 also shows a rotatable carousel 14 which can serially bring a plurality of analytical sample containers such as test tubes 16A, 16B and 16C or the like carried by sample carrier 15 into position for processing by the carriage and transfer to assay trays carried on table 12. When such samples are brought to position for pick up, they can have information, such as contained on bar codes 41A, etc. read by optical scanner 42. In this embodiment, it is important that the bar codes be in the focal plane of the scanner 42.

The sample transfer pipette 17 is a non-positive displacement pipette, that is it operates by applying a vacuum or a pressure to its tip to take up or discharge liquid, as opposed to a positive displacement pipette which acts by means of a piston pushing against or pulling upon the liquid. Pipette 17 is mounted on and translatable vertically with the carriage 11. It is translatable horizontally such as on guide rails by means of a motor driving a belt. The guide rails and belt drive permit pipette 17 to be moved to above sample container (test tube) 16C, etc. located in sample carrier 15 when the sample is rotated into proper position beneath it. Then, the pipette 17's tip 21 can be lowered into the sample liquid by lowering carriage 11. Carriage assembly 11 is translated vertically by a drive mechanism is not shown in the figures. Tip 21 is removable and pipette 17 thus can be translated to a disposal bin not shown to discharge its tip and also to a position above sample carrier 15 where it can pick up a replacement pipette tip 22A, 22B or 22C, etc by friction fit to the nozzle of pipette 17. The volume of pipette 17 is varied to aspirate and discharge liquid by vertically moving a plunger rod. The plunger rod and its activator move horizontally together with pipette 17. The activator moves vertically with head 11 but also is moved vertically independently. By this arrangement, pipette 17 can be raised and lowered to engage and pick up new pipette tips as needed and then with the pipette tip, pick up, transfer, store within and discharge liquid from various levels within the test sample. It can operate in conjunction with liquid level sensing devices to draw from various depths related to the surrface level of the liquid.

The table 12 accommodates a plurality of trays 37, 39 and 40. These trays can be conventional titer trays that include a matrix arrangement of wells into which may be deposited the liquid(s) to be taken up by the pipette tips. In these actions, it may, from time to time by desirable to be able to very closely control the depth from which a sample is taken, for example in blood work ups where it is often of interest to sample serum or plasma layers on the one hand and cell layers on the other, or to be able to closely control the level at which a sample is deposited in a well, for example. As will be shown hereinafter, certain tip arrangements facilitate this close control.

The automatic traversing of the pipette, the rotation of the carousel to bring samples into alignment, and the pick up of the tips by the pipette is subject to the usual variations common with mechanical devices. As shown in FIGS. 2, 3 and 4A and B the sample carrier 15 of this invention is particularly constructed to correct for a number of these variations. Carrier 15 rests on and is carried by carousel 14. Carrier 15 is constructed of two pieces of plastic material, a bottom 204 and a top 205. These pieces are circular in shape with the bottom 204 being raised in the center and the top 205 being depressed in the center. THe top and bottom are joined at their center by welds and by bolted knob 206. The knob also provides a convenient handle for lifting and manipulating the carrier. This arrangement allows the edge of the top 205 to resiliently move upwards and downwards relative to the bottom 204. The bottom 204 has registration means 207 for engaging a raised section 202 of carousel 14 so that when the carousel moves it also moves the carrier.

The carrier 15 has a series of apertures about the outside edge of its top 205. One of these is shown as 209. Corresponding cups or receivers such as 210 are located in bottom 204 below these apertures. These apertures and indents are sized to accept sample containers such as test tube 16A. These tubes are generally conventional blood sample tubes which are commonly available in 11, 12 and 13 mm diameters. It is a feature of this invention that the carrier can accommodate all of these different samples without modification. When the sample tube 16A is inserted into the aperture of the carrier, it contacts a resiliently deflectable finger 211 which is shown having an optional centering button 212 for facilitating the contact with the tube. This elastically deflects the finger 211 such that the finger pushes against the tube. This has the effect of locking the tube against the outside edge of the aperture 209 which is advantageous in that it places the outside edge of the tube in a consistent horizontal focal plane, irrespective of the size of the sample tube. This feature is especially well illustrated in FIGS. 4A and 4B where examples of large and small tubes are illustrated. This allows an optical scanner, such as 42 to read information contained on the surface of the tube, for example, the bar code 41A shown. This also holds the tube in firm alignment so that it can be consistently sampled and so that it bar code 41A will not inadvertently be rotated out of the scanner's view. In the embodiment shown, which is the preferred embodiment, the cup 210 in bottom 204 is directly below the aperture 209 in top 205 so that the test tubes are positioned vertically and essentially perpendicular to the plane of rotation of carousel 14.

The carrier is fabricated from a resilient, i.e. deformable and elastic, material such as stamped metal or vacuum-formed organic polymer sheet. Stamped steel or aluminum or stainless steel are representative metals. Plasticised poly(vinyl chloride), PET (Poly(Ethylene Terphthalate), polystyrene and ABS type copolymers are representative polymers. As an aside, it is generally desired to be able to autoclave these carriers to clean them between uses. The material of construction should, in these cases, be appropriate for such treatment. The deflectable fingers 211 can be formed directly as appendages of the carrier top 205 and can be formed of the same materials as the top, if desired.

The top 205 also carries a plurality of tip-receiving collars 219 from which are suspended the pipette tips such as tip 22A. The top surface of collar 219 is a dimensionally-finished surface which permits the tips to be in a predetermined vertical position for direct pick up by the pipette. The tip 22A includes a tapered tube 24 which takes up, stores and discharges liquid and a tip collar 223 which optionally can carry a plurality (such as from about 4 to about 10) of vertical exterior ribs 224. These ribs can provide strengthening for the collar area and they can also widen the effective diameter of the collar. The tip 22A fits through an aperture 222 in collar 219. The size of this aperture 222 is controlled to be large enough to receive the tapered tube without engagement but small enough to retain the tip collar 223. Commonly and preferably, the diameter of aperture 222 is about 1/16 inch ±1/32 inch larger than the largest exterior diameter of the tapered tube of the pipette tip. Similarly, the outside diameter of the lower end of the tip collar or the effective diameter of the circle created by he ribs 224 is generally at least about ⅛ inch larger than the diameter of aperture 222. This spacing allows the tips to have substantial lateral movement in the apertures and thus permit them to move to accommodate minor variations in the placement of the pipette 17 when it arrives to pick them up or minor variations in the positioning of the carousel. FIGS. 6A, 6B and 6C are a time-sequenced illustration of this process by which a pipette tip can be taken up while compensating for a slight degree of off-centeredness. Another dimension which can be important is the exterior diameter if the bell mouth of the tip collar. If this dimension is larger that the diameter of the pipette 17, itself, it can have the advantageous effect of preventing contact and contamination between the pipette and the sample container and its contents. This relationship is shown in FIG. 2, for example.

An important feature of carrier 15 is its vertical flexibility. As a result of the nonsupported exterior edge of top 205, it can move up and down elastically from about 1/64 inch to about ½ inch when vertical force is applied to collars 219. Thus, when pipette 17 engages a pipette tip 22A in collar 219, this force will cause the top to flex. The flex should be great enough to accommodate variation in pipette travel, and the like but the top should present adequate rigidity to permit the pipette to sealably seat in the tip. Generally, good results are obtained when the carrier is of a rigidity such that the collars flex about 0.020 inches to about 0.060 inches under a weight of about 2½ pounds.

Turning to FIG. 5. a variation of the sample carrier of this invention is shown. This carrier 15A differs from carrier 15 in that cup 210 is not directly below aperture 209 but rather is spaced outward from it so that a test tube placed in the carrier is angled from about 5° to about 45° from vertical and especially from about 20° to about 30° from vertical. This angling is advantageous in that if the carrier is rapidly rotated, centifugal separation of differing density species within the sample can be accomplished. This can be carried out by mounting the carrier on a centrifuge and spinning it. This can be very efficient in that two labor-intensive manual transfers of the samples (in and out of the centifuge carrier) can be eliminated. Although not a requirement, it may facilitate automated pipette tip pick up from an angle carrier such as 15A if the tips 22A to be picked up by pipette 17 are positioned in the carrier at the same angle as the test tubes as is shown in FIG. 5. In this case a ring 250 can support the tips in their angled orientation.

Figures 7, 8, 9:
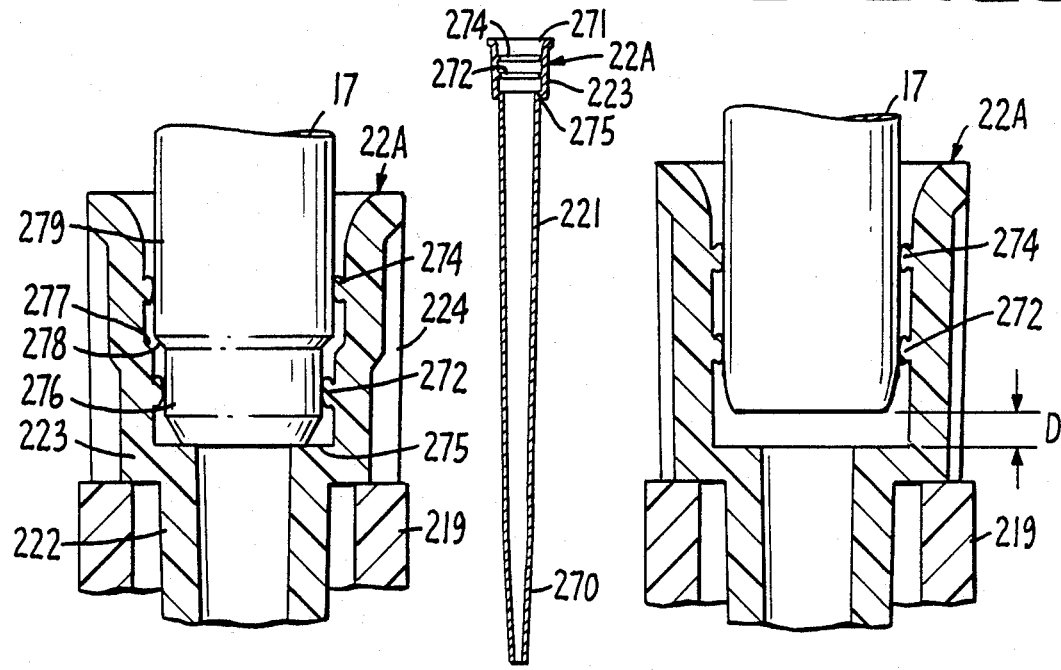
FIG. 7 is a enlarged cross-sectional view of a pipette and part of a tip which illustrate an alternative embodiment of the invention in which the pipette and the pipette tip are each stepped so that the seal and alignment functions are carried out essentially simultaneously.
FIG. 8 is an enlarged cross-sectional view of a pipette and part of a tip which illustrate an additional embodiment of this invention.
FIG. 9 is a somewhat enlarged cross-sectional view of a preferred pipette tip of this invention.

The present invention is designed to facilitate the automatic pick up of pipette tips by automated pipettes. Tips of special interest are elongated tips which can reach to the bottom of a blood tube so as to sample a cell plug located there after centrifugation of a blood sample. Tip lengths of from about 2 to about 3½ inches are generally suitable for such applications. In preferred embodiments, this tip is as shown in FIG. 9 with a relatively narrow cross section tapered tube 221 joining an attachment tip collar 223 at its large end and a more tapered end tube 270 at its small end. The average diameter of the tapered tube 221 should be small, such as from about 1/16 to about 3/16 inch. This will provide minimal displacement of liquid when the tip is lowered into a liquid sample to its full depth. The taper of the tube 221 is generally as small as will permit the tip to be removed from the internal pin during molding (i.e. less than about 1° or so). The tapered end tube 270 is shown with a taper of about 3° or so.

In the tip shown in FIG. 9, and as also shown in FIGS. 6A–6C, the joint between tube 221 and collar 223 can provide a flange 275 which is a positive stop for pipette 17 when it is inserted into the tip. This, in turn provides close control of the depth to which the pipette is inserted and assures that it will be reproducible.

The collar 223 contains on its inner surface a circumferential ring 272 which serves as a seal ring. When the pipette is inserted, ring 272 form an uptake vacuum- and discharge pressure-proof seal with the pipette. Because of the elongated length of the tip 22A, it is possible for it to be skewed when it is attached to the pipette. This can be corrected for or in substantial part eliminated by providing alignment means inside the collar between the seal and the mouth of the collar. This alignment device can be protrusions or the like spaced about the inside of the collar or as shown in FIG. 9 can be a second alignment ring 274 placed circumferentially around the inside of the collar. If desired, this alignment ring can be sized to sealably engage the pipette as well and thus provide a double seal.

As can be best seen in FIGS. 6A–6C, the mouth of the collar 223 is bell-mouthed or flaired. This makes it easier for an automated pipette to engage the tip and eliminates tip feeding jams. The end of pipette 17 is beveled. This serves two purposes. For one, it too makes it easier for the pipette to "find" the mouth of the tip and again eliminates jams. As shown in FIGS. 6A–6C, this works in combination with the size relationship between the pipette tip tube 221 and the carrier collar aperture 222 to facilitate correction for misalignment. The second purpose for the beveled end is to provide a positive "snap" seal mechanism. As the taper pushes against the seal ring 272 there is substantial resistance because of the relative angles of the taper and the seal surface. When the taper clears the seal ring on insertion the force required drops. This means that the pipette completes its insertion with less force and "snaps" to full insertion and into abutment with stop flange 275. If desired, the bevel end can be replaced by a round or radiused end. This design will facilitate the ready joining of the tip to the pipette but it will not provide the "snap" feature as will the bevel design.

In an alternative embodiment, as shown in FIG. 7 the collar of tip 22A and the pipette are each stepped at 277 and 278 respectively on their contacting surfaces so that the region 276 of the pipette 17 which seals with ring 272 is smaller and can clear the guide ring 274 with minimal contact. This makes it possible for surfaces 276 and 279 of the pipette to contact the seal ring 272 and the guide ring 274 at substantially the same point in its travel and thus for the insertion to be faster and with less motion required. This design has additional advantages, as well. Detachment is more rapid than if both the seal and the alignment provisions acted upon the same diameter. In addition, the outermost seal or alignment ring 274 is not stessed by the inner seal-mating surface 276 passing over it, as is the case in the embodiment shown in FIG. 6, for example. This can assure that the outermost ring 274 is not damaged or distorted prior to its actual use.

Again, in the embodiment shown in FIG. 7 the pipette has a beveled end and is inserted into the tip until this end abuts a positive stop 275 at the junction of the collar 223 and the tapered tube 222.

In FIG. 8 an embodiment is shown in which there is no positive stop. The pipette forms its seal with the seal ring 272 and is guided by guide ring 274 but its insertion distance is controlled by setting the pipette drive mechanism to an appropriate travel to provide a preset distance "D". As shown in this FIG., in this embodiment, it may be preferred to use a rounded end rather than a beveled end on the pipette 17 as in this case, where no positive stop is employed, the snap effect provided by the bevel may not be desired when accurate dimensional control is called for.

Although this invention has been described with reference to certain preferred embodiments, it will be appreciated that it can be modified without departing from its spirit and that the scope of the invention is as defined by the following claims.

What is claimed is:

1. In a pipette system having a generally cylindrical pipette nozzle having an attachment end defining a passageway, having an end surface and having an outer generally cylindrical surface which can engage a pipette tip, means for achieving axial movement of said pipette nozzle and a pipette tip having a generally cylindrical inner surface detachably affixed to said pipette nozzle by engagement of said inner surface of the pipette tip with the outer surface of the nozzle in fluid communication with said passageway; the improvement comprising employing as said pipette nozzle a pipette nozzle having an outer surface defining a plurality of generally cylindrical pipette nozzle sections each having a nozzle section height and a nozzle section diameter, said nozzle section diameter for each of said pipette nozzle sections being different from that of the others with the generally cylindrical pipette nozzle section of smallest nozzle section diameter being adjacent to the end surface of said nozzle and the other generally cylindrical pipette nozzle sections positioned in order of increasing nozzle section diameter away from the end surface and employing as said tip a disposable pipette tip comprising an elongated truncated conical double open-ended tube section having a small end defining a passageway for vacuum uptake and pressure discharge of liquid and a large end joined to and in fluid communication with a first end of a pipettereceiving collar portion extending radially away from the conical tube section, said collar portion having a bell mouthed opening at its second end and an inner surface defining a plurality of generally cylindrical tip sections each having a tip section height and a tip section diameter different from that of the others with the generally cylindrical tip section having of largest diameter being adjacent to the bell mouthed opening and the other generally cylindrical tip sections positioned in order of decreasing tip section diameter toward the first end of the collar the tip section height and tip section diameter of each of the tip sections being related to the nozzle section height and nozzle section diameter of a nozzle section so as to permit nestling insertion of said nozzle into the collar of said tip, at least two of said plurality of generally cylindrical tip sections each carrying an inward-extending circumferential sealing rib, the at least two ribs being axially displaced from one another, being integral with the collar portion and capable of deforming in contact with a generally cylindrical collar section to give a vacuum uptake and pressure discharge seal upon direct nontwisting axial insertion of the nozzle of said pipette into the collar portion via its bell mouthed open end.

2. The improved pipette system of claim 1 wherein said plurality is two.

3. The improved pipette system of claim 1 additionally comprising an inward-extending circumferential shoulder stop located on the inner surface of the collar portion between the sealing ribs and the first end of the collar said stop engaging said end surface of the pipette nozzle and limiting the depth of said direct nontwisting axial insertion of said nozzle into said collar portion of said pipette tip.

4. The improved pipette system of claim 3 wherein the inward-extending circumferential shoulder stop is defined by the large end of the conical tube section having a smaller inside diameter than the inside diameter of the collar portion at the point at which said tube and said collar join.

5. The improved pipette system of claim 4 wherein said plurality is two.

* * * * *